United States Patent
Pruehs et al.

(10) Patent No.: US 8,658,827 B2
(45) Date of Patent: Feb. 25, 2014

(54) METHOD FOR SYNTHESIZING SUBSTITUTED AMINOCYCLOHEXANONE COMPOUNDS

(75) Inventors: Stefan Pruehs, Neuss (DE); Carsten Griebel, Aachen (DE); Marita Mueller, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 13/313,902

(22) Filed: Dec. 7, 2011

(65) Prior Publication Data

US 2012/0149914 A1     Jun. 14, 2012

Related U.S. Application Data

(60) Provisional application No. 61/420,979, filed on Dec. 8, 2010.

(30) Foreign Application Priority Data

Dec. 8, 2010 (EP) .................. 10015428

(51) Int. Cl.
C07C 211/01 (2006.01)
C07D 495/12 (2006.01)
(52) U.S. Cl.
USPC .......................... 564/307; 548/430
(58) Field of Classification Search
None
See application file for complete search history.

(56) References Cited

U.S. PATENT DOCUMENTS

| | | | | |
|---|---|---|---|---|
| 8,138,187 B2 * | 3/2012 | Zemolka et al. | ............... | 514/247 |
| 8,288,430 B2 * | 10/2012 | Zemolka et al. | ............... | 514/409 |
| 8,293,758 B2 * | 10/2012 | Zemolka et al. | ............... | 514/278 |
| 2009/0000294 A1 * | 1/2009 | Misselhorn | ............... | 60/517 |
| 2009/0156593 A1 | 6/2009 | Zemolka et al. | | |
| 2010/0048553 A1 | 2/2010 | Schunk et al. | | |
| 2010/0048554 A1 | 2/2010 | Schunk et al. | | |
| 2010/0240897 A1 | 9/2010 | Hinze et al. | | |

FOREIGN PATENT DOCUMENTS

| | | |
|---|---|---|
| DE | 10 2007 009 235 A1 | 9/2008 |
| WO | WO 2004/043967 A1 | 5/2004 |
| WO | WO 2005/070407 A1 | 8/2005 |
| WO | WO 2006/010094 A1 | 1/2006 |
| WO | WO 2006/010095 A2 | 1/2006 |
| WO | WO 2008/009416 A1 | 1/2008 |
| WO | WO 2008/101660 A1 | 8/2008 |

OTHER PUBLICATIONS

Lednicer et al., "4-Amino-4-arylcyclohexanones and Their Derivatives, a Novel Class of Analgesics. 1. Modification of the Aryl Ring", 1981, Journal of Medicinal Chemistry, pp. 341-346, vol. 24 (seven (7) sheets).
Lednicer et al., "4-(p-Bromophenyl)-4-(dimethylamino)-1-phenethylcyclohexanol, an Extremely Potent Representative of a New Analgesic Series", 1979, Journal of Medicinal Chemistry, pp. 1157-1158, vol. 22 (two (2) sheets).
European Search Report with partial English translation dated May 18, 2011 (seven (7) sheets).
Lednicer et al., "4-Aryl-4-aminocyclohexanones and Their Derivatives, a Novel Class of Analgesics. 3. m-Hydroxyphenyl Derivatives", 1981, Journal of Medicinal Chemistry, pp. 341-346, vol. 24 (six (6) sheets).
International Preliminary Report on Patentability (PCT/IB/373) including Written Opinion (PCT/ISA/237) dated Jun. 20, 2013 {Five (5) Pages}.
International Search Report dated Feb. 8, 2012 {Four (4) Pages}.

* cited by examiner

*Primary Examiner* — Nyeemah A Grazier
(74) *Attorney, Agent, or Firm* — Crowell & Moring LLP

(57) ABSTRACT

A method of synthesizing a substituted aminocyclohexanone compound comprising reacting a compound of formula (II)

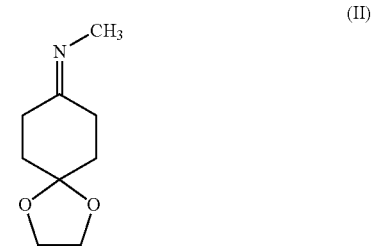

with an organolithium compound to form a compound of formula (III)

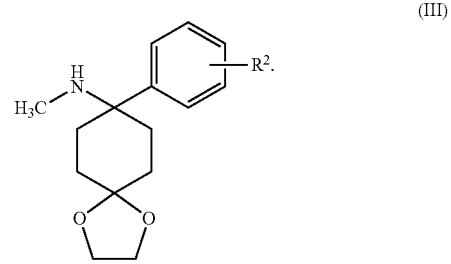

12 Claims, 1 Drawing Sheet

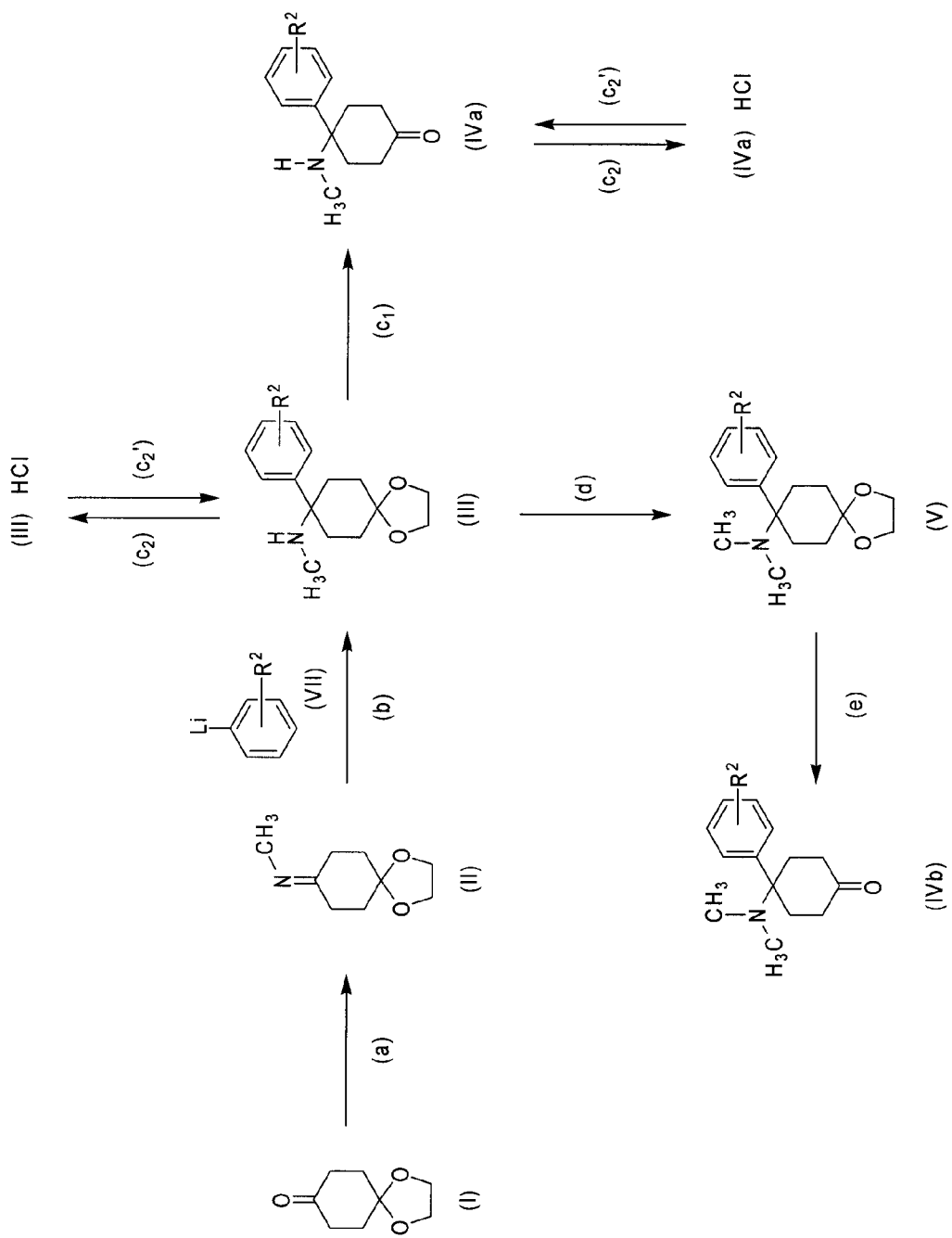

METHOD FOR SYNTHESIZING SUBSTITUTED AMINOCYCLOHEXANONE COMPOUNDS

CROSS REFERENCE TO RELATED APPLICATIONS

This application claims priority from U.S. provisional patent application No. 61/420,979, filed Dec. 8, 2010. Priority is also claimed based on European patent application no. EP 10 015 428.5, filed Dec. 8, 2010.

BACKGROUND OF THE INVENTION

The invention relates to a method of synthesizing substituted aminocyclohexanone derivatives.

Substituted aminocyclohexanone derivatives are known from WO 2004/043967 as important intermediates in the synthesis of spirocyclic cyclohexane derivatives. It is also known that some spirocyclic cyclohexane derivatives have an affinity for the μ-opioid receptor and the ORL1 receptor and are suitable as active ingredients in drugs, in particular for the treatment of pain of disorders of the central nervous system.

The production methods described in WO 2004/043967 for synthesis of the corresponding substituted aminocyclohexanone intermediates require the use of cyanide salts.

Further production methods which include the use of cyanide salts are known from WO 2008/101660, WO 2008/009416, Lednicer, J. Med. Chem. 1981, 24, 341-346, and Lednicer, J. Med. Chem. 1979, 22, 1157-1158.

Other production methods include the use of azide salts (WO 2006/010095, WO 2006/010094, WO 2005/070407).

A further known production method includes eight synthesis stages and also requires the use of azide salts within the scope of a Curtius reaction (Lednicer et al., J. Med. Chem. 1980, 23, 424-430).

However, the use of cyanide salts or azide salts is disadvantageous, inter alia, because production on a commercial scale is hindered for reasons of occupational safety and environmental protection.

There is a need for a method of production of substituted aminocyclohexanone derivatives which affords advantages over conventional methods and which, in particular, does not require the use of cyanide salts or azide salts.

SUMMARY OF THE INVENTION

The object of the invention is therefore to provide an improved method of producing substituted aminocyclohexanone compounds.

Another object is to provide a method of producing substituted aminocyclohexanone compounds which can be carried out at a gram or kilogram scale.

A further object is to provide a method of producing substituted aminocyclohexanone compounds which can be carried out without the use of cyanide salts.

An additional object is to provide a method of producing substituted aminocyclohexanone compounds which can be carried out in as few synthesis stages as possible.

It is also an object of the invention to provide a method of producing substituted aminocyclohexanone compounds which can be carried out in a cost-effective manner.

Yet another object of the invention is to provide a method of producing substituted aminocyclohexanone compounds which produces good yields.

These and other objects have been achieved by the invention as described and claimed hereinafter.

It has surprisingly been found that the synthesis of substituted aminocyclohexanone derivatives of general formula (IV)

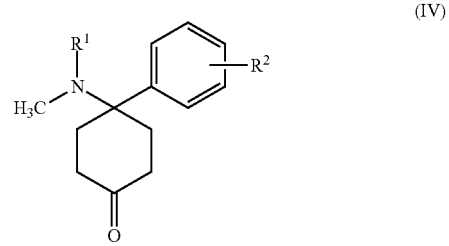

(IV)

in which
R$^1$ stands for —H or —CH$_3$, and
R$^2$ stands for —H, —Cl or —F;
is possible by a method comprising the following step
(b) reaction of a compound of formula (II)

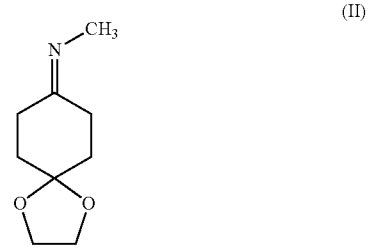

(II)

with an organolithium compound of general formula (VII)

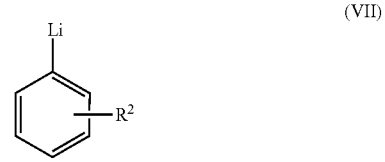

(VII)

in which R$^2$ stands for —H, —Cl or —F;
to form a compound of general formula (III)

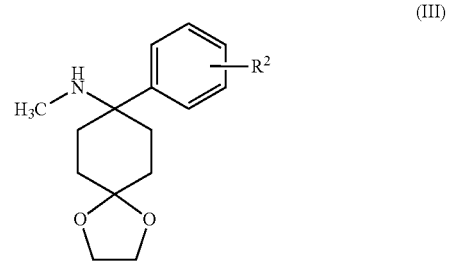

(III)

and conversion of the compound of general formula (III) into the compound of general formula (IV) by optional methylation of the amino function and cleaving of the ketal function.

It has surprisingly been found that compounds of general formula (IV) can be synthesised in few synthesis stages and with good overall yields, without the use of cyanide salts or azide salts.

It has surprisingly been found that organolithium compounds can be added directly to imines of formula (II) and that the intermediate stage of the amino nitrile described in WO 2004/043967 can thus be avoided.

The organolithium compound is selected from the group consisting of phenyllithium, 4-fluorophenyllithium and 4-bromophenyllithium; phenyllithium is particularly preferred, that is to say $R^2$ is preferably H.

In a preferred embodiment, a molar excess of the compound of formula (II) is used.

In another preferred embodiment, a molar excess of the organolithium compound of general formula (VII) is used.

In a further preferred embodiment, equimolar amounts of the compound of formula (II) and of the organolithium compound of general formula (VII) are used.

At least 1.0 equivalent of the organolithium compound of general formula (VII) is preferably used, more preferably at least 1.025 equivalents, even more preferably approximately 1.05 equivalents, in each case based on the amount of substance of the compound of formula (II).

The compound of formula (II) is preferably reacted with the organolithium compound of general formula (VII), preferably phenyllithium, in inert solvents, preferably in dibutyl ether, diethyl ether, tetrahydrofuran or toluene.

The compound of formula (II) is preferably reacted with the organolithium compound of general formula (VII) at a temperature of 200° C. at most, more preferably of 100° C. at most, even more preferably of 60° C. at most, most preferably at temperatures between 0° C. and 35° C., in particular at room temperature.

The compound of formula (II) is preferably reacted with the organolithium compound of general formula (VII) with stirring.

In a preferred embodiment, the compound of formula (II) is provided, preferably in a solvent, and the organolithium compound of general formula (VII) is added.

In another preferred embodiment, the organolithium compound of general formula (VII) is provided, preferably in a solvent, and the compound of formula (II) is added.

In a preferred embodiment, the compound of general formula (III) is reacted further without prior purification. In another preferred embodiment, the compound of general formula (III) is first isolated before it is reacted further.

In a preferred embodiment of the method according to the invention, the compound of formula (II) is obtained by the following step (a) reaction of a compound of formula (I)

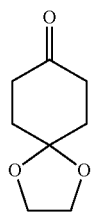

(I)

with methylamine.

Step (a) is thus preferably carried out chronologically before step (b). In a preferred embodiment, step (b) is carried out chronologically immediately after step (a), wherein the compound of general formula (II) is, however, purified beforehand if necessary.

The reaction preferably takes place in methanol, ethanol or THF. The reaction preferably takes place in ethanol, preferably at room temperature.

At least 1.0 equivalent of methylamine is preferably used, more preferably at least 1.5 equivalents, even more preferably at least 2.0 equivalents, in each case based on the amount of substance of the compound of formula (I).

In a preferred embodiment, the compound of general formula (II) is reacted further without prior purification. In another preferred embodiment, the compound of general formula (II) is first isolated before it is reacted further.

In a preferred embodiment, the method according to the invention comprises the following step ($c_1$) cleaving of the ketal function of the compound of general formula (III) to obtain the compound of general formula (IVa),

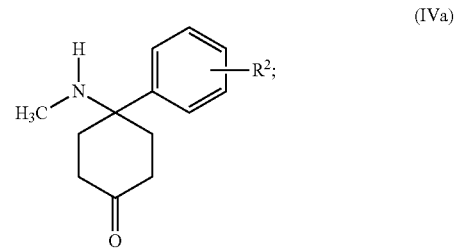

(IVa)

that is to say the compound of general formula (IV), in which $R^1$ stands for —H.

Step ($c_1$) is thus preferably carried out chronologically after step (b). In a preferred embodiment, step ($c_1$) is preferably carried out chronologically immediately after step (b), wherein the compound of general formula (III) is, however, purified beforehand if necessary.

The ketal function is cleaved by known methods. The ketal function is preferably cleaved in an acid-catalysed manner in the presence of a molar excess of water.

The ketal function may be cleaved with the addition of an organic solvent in the presence of 20 to 100 mol % water. The ketal function is more preferably cleaved in water as a solvent.

Other methods known in the literature, such as the method known from Lednicer et al., J. Med. Chem. 1980, 23, 424-430, may in this instance do completely without the use of methanol, which is poisonous, as a solvent.

The ketal function is preferably cleaved at a pH value of 3 at most, more preferably 2.5 at most, most preferably in the range of 0 to 2, and in particular of 0.5 to 1.5.

Suitable catalysts are mineral acids, such as hydrochloric acid, sulfuric acid, nitric acid or phosphoric acid; organic acids such as para-toluene sulfonic acid, benzene sulfonic acid, methane sulfonic acid, trifluoromethane sulfonic acid, formic acid, acetic acid or oxalic acid; acid ion exchangers; lanthanide salts; or enzymes. A mineral acid or an organic acid is preferably used as a catalyst.

The ketal function is most preferably cleaved in the presence of hydrochloric acid, preferably at temperatures of 20° C. to 100° C., more preferably at temperatures of 40° C. to 80° C.

In a preferred embodiment, the compound of general formula (IVa) is reacted further without prior purification. In another preferred embodiment, the compound of general formula (IVa) is first isolated before it is reacted further.

In a preferred embodiment, the method according to the invention comprises the following step:

(c₂) conversion of the compound of general formula (III) or (IVa) into the hydrochloride.

Step (c₂) is thus preferably carried out chronologically after step (b) or (c₁). In a preferred embodiment, step (c₂) is carried out chronologically immediately after step (b), wherein the compound of general formula (III) is, however, purified beforehand if necessary. In another preferred embodiment, step (c₂) is carried out chronologically immediately after step (c₁), wherein the compound of general formula (IVa) is, however, purified beforehand if necessary.

In a preferred embodiment, the compound of general formula (III) is converted into the hydrochloride. In another preferred embodiment, the compound of general formula (IVa) is converted into the hydrochloride.

The compound of general formula (III) or (IVa) is preferably converted into the hydrochloride with the use of gaseous hydrogen chloride in the presence of a solvent. In particular, acetone, 2-butanone or isopropanol are suitable as solvents.

In a preferred embodiment, the hydrochloride of the compound of general formula (III) or (IVa) is reacted further without prior purification. The compound of general formula (III) or (IVa) is preferably first isolated, however, before it is reacted further.

The compound of general formula (III) or (IVa) can be released from the hydrochloride as a free base by adding sodium hydroxide solution (step (c₂')). Step (c₂') is thus preferably carried out chronologically after step (c₂). In a preferred embodiment, step (c₂') is carried out chronologically immediately after step (c₂), wherein the hydrochloride of the compound of general formula (III) or (IVa) is, however, purified beforehand if necessary.

The free base is particularly preferably released in the presence of 2-methyltetrahydrofuran (2-MTHF).

In a preferred embodiment, the method according to the invention comprises the sequence of step (c₂) followed by (c₂') as a purification step. For this purpose, the compound of general formula (III) or (IVa) is first converted into the hydrochloride by means of step (c₂), isolated and then converted back into the form of the free base in step (c₂').

In a preferred embodiment, the method according to the invention comprises the following step (d) methylation of the amino function of the compound of general formula (III) to obtain the compound of general formula (V)

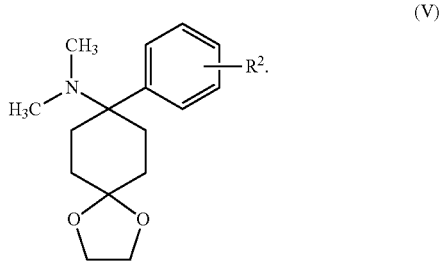

(V)

Step (d) is thus preferably carried out chronologically after step (b), optionally chronologically after the sequence of steps (b), (c₂) and (c₂'). In a preferred embodiment, step (d) is carried out chronologically immediately after step (b), wherein the compound of general formula (III) is, however, purified beforehand if necessary. In another preferred embodiment, step (d) is carried out chronologically immediately after step (c₂'), wherein the compound of general formula (III) is, however, purified beforehand if necessary.

The amino function is preferably methylated (n-methylation) by reductive amination.

In a particularly preferred embodiment, the reductive amination is carried out by reacting the compound of general formula (III) with formaldehyde in the presence of formic acid (Eschweiler-Clarke reaction).

In contrast to methods known in the literature, in which metal hydrides such as lithium aluminium hydride are used (for example Lednicer et al., J. Med. Chem. 1980, 23, 424-430), the use of formic acid as a reducing agent affords the advantage that it is not flammable, can be handled more easily in particular on an industrial scale, and does not leave behind any metal residues in the product.

The n-methylation is preferably carried out in the presence of a molar excess of formaldehyde, preferably in the form of a formaldehyde solution, and of a molar excess of formic acid.

At least 1.5 equivalents of formic acid are preferably used, more preferably at least 2.0 equivalents, most preferably at least 2.5 equivalents, and in particular preferably at least 3.0 equivalents, based on the amount of substance of the compound of general formula (III).

At least 1.0 equivalent of formaldehyde is preferably used, more preferably at least 1.05 equivalents, in particular preferably at least 1.1 equivalents, based on the amount of substance of the compound of general formula (III).

At most, 2.0 equivalents of formaldehyde are preferably used, more preferably at most 1.5 equivalents, in particular preferably at most 1.25 equivalents based on the amount of substance of the compound of general formula (III).

In another preferred embodiment, the reductive amination takes place by reacting the compound of general formula (III) with formaldehyde and subsequent reduction of the iminium ion, formed in situ, with hydrogen in the presence of a hydrogenation catalyst.

In a further preferred embodiment, the reductive amination takes place by reacting the compound of general formula (III) with formaldehyde and subsequent reduction of the iminium ion, formed in situ, with the aid of a complex hydride, such as sodium borohydride.

The n-methylation may also take place by adding methylation reagents, such as methyl iodide, dimethyl sulfate or dimethyl carbonate.

In a preferred embodiment, the compound of general formula (V) is reacted further without prior purification. In another preferred embodiment, the compound of general formula (V) is first isolated before it is reacted further.

In a preferred embodiment, the method according to the invention comprises the following step (e) cleaving the ketal function of the compound of general formula (V) to obtain the compound of general formula (IVb)

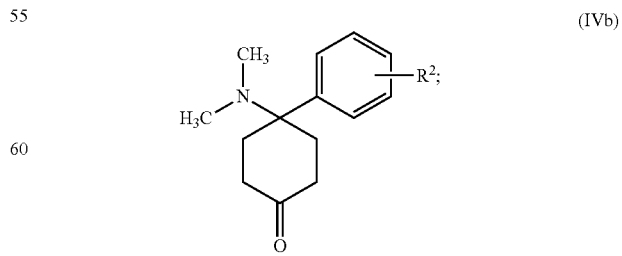

(IVb)

that is to say the compound of general formula (IV), in which R¹ stands for —CH₃.

Step (e) is thus preferably carried out chronologically after step (d). In a preferred embodiment, step (e) is carried out chronologically immediately after step (d), wherein the compound of general formula (V) is, however, purified beforehand if necessary.

The ketal function is preferably cleaved similarly to the preferred conditions for step ($c_1$).

The ketal function is most preferably cleaved in the presence of hydrochloric acid at temperatures of 40° C. to 80° C.

The free base of the compound of general formula (IVb) is preferably obtained once the ketal function has been cleaved in acid solution by adding aqueous sodium hydroxide solution. The solution is preferably brought to a pH value of ≥8, more preferably ≥10, most preferably ≥12. The free base is preferably released in the presence of 2-methyltetrahydrofuran or tetrahydrofuran.

The compound of general formula (IVb) can be purified by recrystallisation from isopropanol/water.

The method according to the invention affords the advantage that compounds of general formula (IV) can be synthesised, without the use of cyanide salts or azide salts, in few synthesis stages and with good overall yields.

Expensive and time-consuming purification steps, such as chromatography methods, can be dispensed with completely, in particular on an industrial scale. Instead, the method according to the invention implements one or more crystallisation steps to purify the intermediate and/or end products.

Compared to the method known from Lednicer et al., J. Med. Chem. 1980, 23, 424-430, the overall yield is more than twice as high. In addition, it is possible to dispense with the use of methanol, which is poisonous, as a solvent.

It has also surprisingly been found that the synthesis of spirocyclic cyclohexane derivatives of general formula (VI)

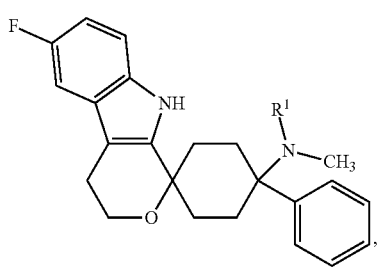

in which
$R^1$ stands for —H or —CH$_3$ or of a physiologically acceptable salt is possible by a method comprising the method of synthesizing a compound of general formula (IV) and an acid-catalysed Oxa-Pictet-Spengler reaction of the compound of general formula (IV) with a heteroaromatic compound to form the compound of general formula (VI).

The compounds of general formula (VI) can be obtained similarly to the method known from WO 2004/043967 by reacting compounds of general formula (IV) with heteroaromatic compounds of general formula (Het) with the addition of acid or the trimethylsilyl esters thereof:

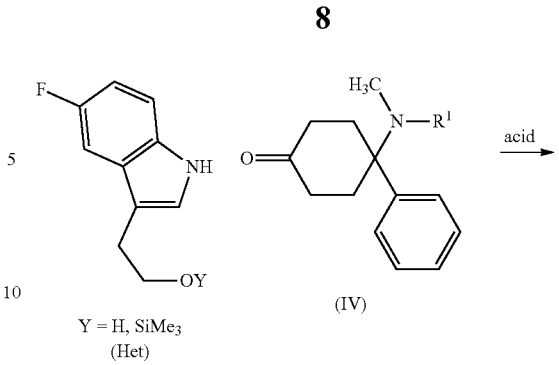

Y = H, SiMe$_3$
(Het)

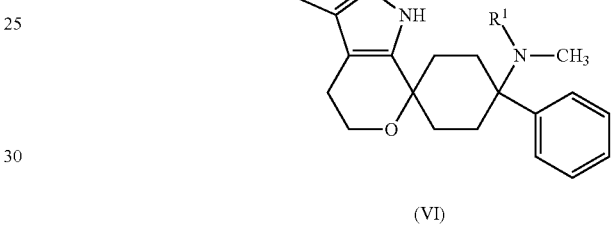

A further aspect of the invention thus relates to a method of synthesizing compounds of general formula (VI) or the physiologically acceptable salts thereof, comprising the steps (a), (b), ($c_1$), ($c_2$), ($c_2'$), (d) and/or (e).

A preferred embodiment relates to a method of synthesizing the compound of formula (VIa), that is to say a compound of general formula (VI) in which $R^1$ stands for —H, or a physiologically acceptable salt thereof

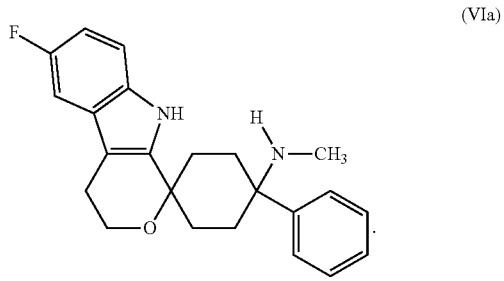

The method of synthesizing the compound of formula (VIa) preferably comprises the steps (a), (b), ($c_1$), and optionally ($c_2$) and optionally ($c_2'$).

Another preferred embodiment relates to a method of synthesizing the compound of formula (VIb), that is to say a compound of general formula (VI) in which (VI) $R^1$ stands for —CH$_3$, or a physiologically acceptable salt thereof

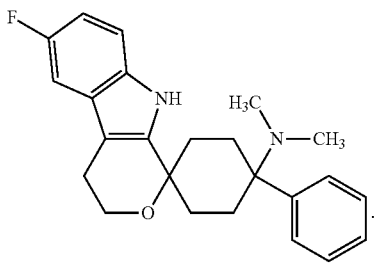

(VIb)

The method of synthesizing the compound of general formula (VIb) preferably comprises the steps (a), (b), (d) and (e), and preferably also steps (c₂) and (c₂').

For the purposes of the description, physiologically acceptable salts of the compounds according to the invention are provided as salts with anions or acids of the respective compound with inorganic or organic acids which are physiologically acceptable, in particular with use in humans and/or mammals.

Examples of physiologically acceptable salts of some acids are salts of: hydrochloric acid, hydrobromic acid, sulfuric acid, methane sulfonic acid, formic acid, acetic acid, oxalic acid, succinic acid, malic acid, tartaric acid, mandelic acid, fumaric acid, lactic acid, citric acid, glutamic acid, saccharin acid, monomethyl sebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride, citrate and hemicitrate are particularly preferred.

BRIEF DESCRIPTION OF THE DRAWING

The invention will be described in further detail hereinafter with reference to illustrative preferred embodiments depicted in the accompanying drawing FIGURE, which is a schematic illustration of reaction schemes according to the present invention.

DETAILED DESCRIPTION OF EMBODIMENTS

The accompanying drawing FIGURE shows preferred variants of the method according to the invention. Compounds of general formula (IVa), that is to say compounds of general formula (IV) in which $R^1$ stands for H, are preferably synthesised by the chronological sequence of steps (a), (b) and (c₁). In a preferred embodiment, the method additionally comprises step (c₂) and optionally (c₂').

Compounds of general formula (IVb), that is to say compounds of general formula (IV) in which $R^1$ stands for $CH_3$, are preferably synthesised by the chronological sequence of steps (a), (b) (d) and (e). In a preferred embodiment, the method additionally comprises steps (c₂) and (c₂'). In this case the method comprises the chronological sequence of steps (a), (b), (c₂), (c₂'), (d) and (e), and the hydrochloride of the compound of general formula (III) obtained in the meantime in step (c₂) is preferably isolated.

The following examples serve to illustrate the invention, but are not intended to be limiting in terms of their scope.

Example 1

4-(dimethylamino)-4-phenyl-cyclohexanone a) N-(1,4-dioxaspiro-[4,5]-decan-8-yliden)-methanamine Synthesis of the Imine
Cyclohexane dion monoethylene ketal (50 g, 0.32 mol) was mixed with methylamine solution (8 M in ethanol, 100 ml, 0.80 mol) and then with ethanol (100 ml). The batch was stirred for 2-24 h at room temperature. The ethanol was distilled off at 40-45° C. at reduced pressure.
Yield: 98-100% b) N-methyl-8-phenyl-1,4-dioxaspiro[4.5]decan-8-amine

Addition of phenyllithium to the Imine Formed under a)
N-(1,4-dioxaspiro-[4,5]-decan-8-yliden)-methanamine (43 g, 0.25 mol) was dissolved in dibutyl ether (75 ml) and added at room temperature (15-32° C.) to a solution of phenyllithium in dibutyl ether (1.8 M, 149 ml, 0.27 mol). The batch was stirred at room temperature for 1 h. A saturated ammonium chloride solution (60 ml) was then added. The organic phase was concentrated at 75° C. The remaining raw product was used in the next step without purification.

c) Conversion into the Hydrochloride

The residue (N-methyl-8-phenyl-1,4-dioxaspiro[4.5]decan-8-amine) was taken up in 1.5 times the amount of isopropanol and gassed with hydrogen chloride. It was stirred for up to 16 h at 5-25° C. The precipitated hydrochloride was filtered off, washed with isopropanol and dried at increased temperature under vacuum.
Yield: approximately 25% (over steps b) and c))

d) N,N-dimethyl-8-phenyl-1,4-dioxaspiro-[4.5]decan-8-amine

Eschweiler-Clarke Reaction
N-methyl-8-phenyl-1,4-dioxaspiro[4.5]decan-8-amine hydrochloride (15 g, 59 mmol) was taken up in water (37 ml) and 2-methyltetrahydrofuran (57 ml). The free base was released by adding NaOH aq (32%, to pH>12). The organic phase was concentrated at 45° C. at reduced pressure (<10 mbar). The residue was taken up in isopropanol (8 ml) and added dropwise to formic acid (7 ml, 0.19 mol) at up to 65° C. At 65° C., formaldehyde solution (5.8 g, 0.1 mol) was added swiftly and the batch was stirred overnight (approximately 16 h) at 65° C. The batch was concentrated at 80° C. and approximately 20 mbar. The remaining raw product was used in the next step without purification.

e) 4-(dimethylamino)-4-phenyl-cyclohexanone

Cleaving of the Ketal Function
The residue (N,N-dimethyl-8-phenyl-1,4-dioxaspiro-[4.5]decan-8-amine) was taken up in aqueous HCl at pH 1. It was stirred for 1 hour at 65° C. The batch was cooled and brought to pH 4 with NaOH solution. 2-MTHF (52 ml) was then added. The mixture was alkalised with NaOH at 15-25° C. to pH≥12. The organic phase was concentrated at 45° C. and at reduced pressure (<10 mbar). The residue was dissolved at 65° C. in twice the amount of isopropanol/$H_2O$ 60/40. The batch was stirred overnight at −10° C. The precipitate was suctioned off, subsequently washed with cold isopropanol/H₂O and dried overnight in a drying cupboard (45° C., <100 mbar).

Yield: approximately 70% (over steps d) and e))

Example 2

4-(methylamino)-4-phenyl-cyclohexanone

Addition of Phenyllithium to the Imine Formed in Accordance with Example 1a)

N-(1,4-dioxaspiro[4,5]-decan-8-yliden)-methanamine (43 g, 0.25 mol) was dissolved in dibutyl ether (75 ml) and added at room temperature (15-32° C.) to a solution of phenyllithium in dibutyl ether (1.8 M, 149 ml, 0.27 mol). The batch was stirred at room temperature for 1 h.

Processing and Simultaneous Cleaving of the Ketal Function 300 ml of 8% hydrochloric acid were then added dropwise and stirred for 1 hour at 65° C. The organic phase was separated. The batch was cooled and alkalised with NaOH solution at 15-25° C. to pH≥12. It was extracted with 3*100 ml 2-methyltetrahydrofuran and the purified organic phases were concentrated at 45° C. at reduced pressure (<10 mbar).

Conversion into the Hydrochloride

The residue was taken up in 1.5 times the amount of isopropanol and gassed with hydrogen chloride. It was stirred for up to 16 h at 5-25° C. The precipitated hydrochloride was filtered off, washed with isopropanol and dried at increased temperature under vacuum.

Yield: 23-30 g (20-25% based on N-(1,4-dioxaspiro-[4,5]-decan-8-yliden)methanamine).

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A method of synthesizing a compound of formula (IV)

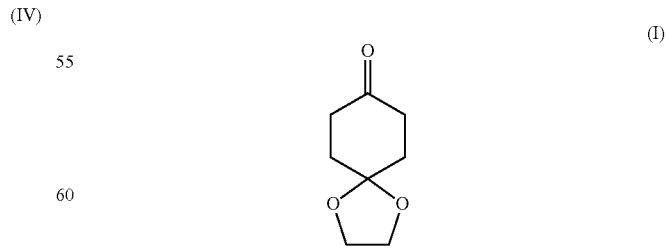

wherein
$R^1$ denotes —H or —CH₃, and
$R^2$ denotes —H, —Cl or —F;

said method comprising reacting a compound of formula (II)

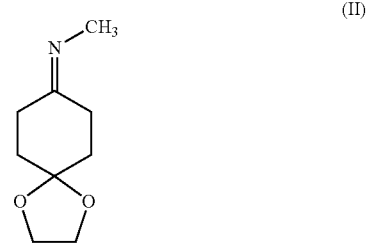

with an organolithium compound of formula (VII)

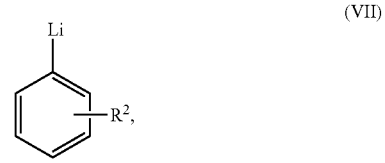

wherein
$R^2$ denotes —H, —Cl or —F;
to form a compound of formula (III)

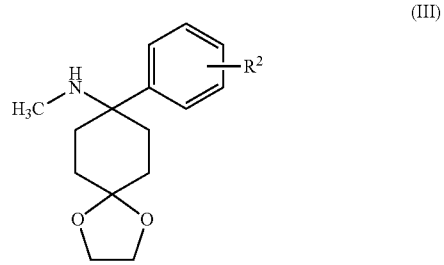

optionally methylating the amino function to obtain a compound in which $R^1$ is CH₃, and
cleaving the ketal function of the compound of formula (III) to convert the compound of formula (III) into the compound of formula (IV).

2. The method according to claim 1, wherein $R^2$ denotes —H.

3. The method according to claim 1, comprising forming the compound of formula (II) by first reacting a compound of formula (I)

(I)

with methylamine.

4. The method according to claim 1, further comprising converting the compound of formula (III) into a hydrochloride salt.

5. The method according to claim 1, further comprising converting a hydrochloride salt of a compound of formula (III) into a free base.

6. The method according to claim 1, wherein the ketal function of the compound of formula (III) is cleaved to obtain a compound of formula (IVa)

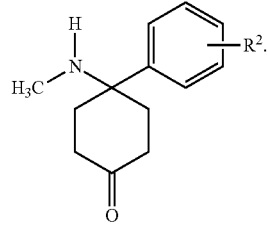

(IVa)

7. The method according to claim 6, further comprising converting the compound of formula (IVa) into a hydrochloride salt.

8. The method according to claim 6, further comprising converting a hydrochloride salt of a compound of formula (IVa) into a free base.

9. The method according to claim 1, wherein the amino function of the compound of formula (III) is methylated to obtain a compound of formula (V)

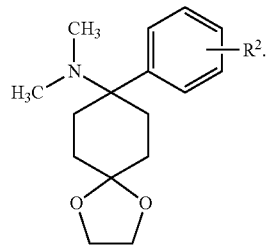

(V)

10. The method according to claim 9, wherein the methylation is effected by reacting the compound of formula (III) with formaldehyde solution and formic acid.

11. The method according to claim 9, wherein the ketal function of the compound of formula (V) is cleaved to obtain a compound of formula (IVb)

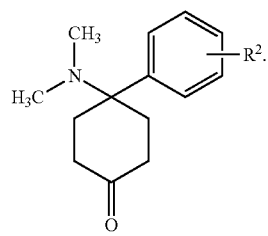

(IVb)

12. A method of synthesizing a compound of formula (VI)

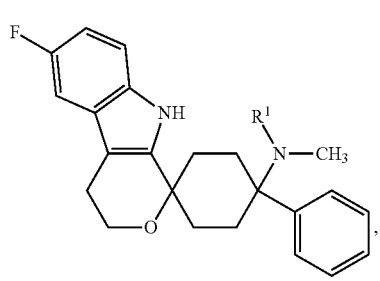

(VI)

wherein
$R^1$ denotes —H or —CH$_3$,
or a physiologically acceptable salt thereof,
said method comprising
reacting a compound of formula (II)

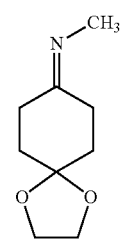

(II)

with an organolithium compound of formula (VII)

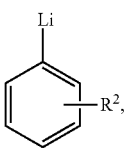

(VII)

wherein
$R^2$ denotes —H, —Cl or —F;
to form a compound of formula (III)

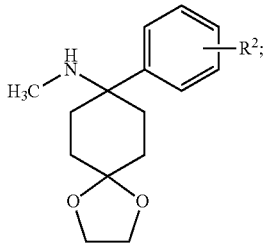

(III)

optionally methylating the amino function to obtain a compound in which $R^1$ is CH$_3$;
cleaving the ketal function of the compound of formula (III) to convert the compound of formula (III) into a compound of formula (IV)

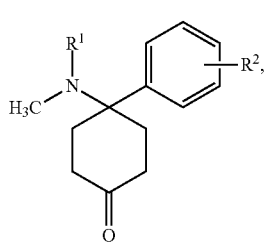 (IV)
and
subjecting the compound of formula (IV) to an acid-catalysed Oxa-Pictet-Spengler reaction with a heteroaromatic compound to form the compound of formula (VI).
* * * * *